United States Patent [19]

Watson

[11] Patent Number: 4,801,292

[45] Date of Patent: Jan. 31, 1989

[54] MEDICAL PUMP FOR DEBRIS COLLECTION

[75] Inventor: Jeremy P. Watson, Clacton-on-Sea, United Kingdom

[73] Assignee: Bard Limited, Sunderland, England

[21] Appl. No.: 65,563

[22] Filed: Jun. 23, 1987

[30] Foreign Application Priority Data

Jun. 24, 1986 [GB] United Kingdom ............... 8615437

[51] Int. Cl.$^4$ .............................................. A61M 5/18
[52] U.S. Cl. ....................................... 604/36; 604/185
[58] Field of Search ............................... 604/131–133, 604/73.74, 35–41, 185

[56] References Cited

U.S. PATENT DOCUMENTS

| | | | |
|---|---|---|---|
| 877,926 | 2/1908 | Hilker | 604/37 |
| 1,925,230 | 9/1933 | Buckholt | 128/231 |
| 3,785,380 | 1/1974 | Brumfield | 604/902 |
| 3,892,226 | 7/1975 | Rosen | 604/37 |

FOREIGN PATENT DOCUMENTS 2136690 9/1984 United Kingdom .

OTHER PUBLICATIONS

Davol–"Single Use Ellik Evacuator", Davol Inc; Cranston, Rhode Island 02920.

*Primary Examiner*—C. Fred Rosenbaum
*Assistant Examiner*—J. L. Kruter
*Attorney, Agent, or Firm*—Dennison, Meserole, Pollack & Scheiner

[57] ABSTRACT

A medical pump comprising an intake/discharge nozzle, a fluid circulator, an elongate barrel extending between and joining the nozzle and circulator, a flushing path and an efflux path peripherally about the flushing path connecting the circulator and nozzle, non-return valves within the paths providing for uni-directional flow from the nozzle through the efflux path to the circulator and from the circulator through the flushing path to the nozzle. A debris-collecting filter element is disposed within the efflux path within the barrel. The filter element and valves may be in the form of a replaceable cartridge. The valves may be constructed as a shuttle with joined oppositely operating valve plates. The valves may also comprise a resilient flap member with a flap formed therein, both the flap member and flap being independently operable and defining the two valves.

14 Claims, 4 Drawing Sheets

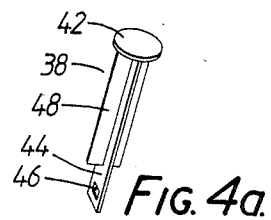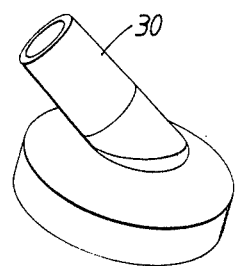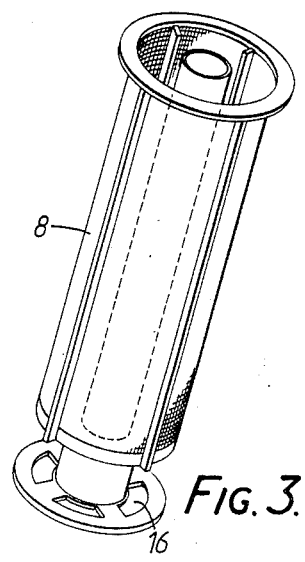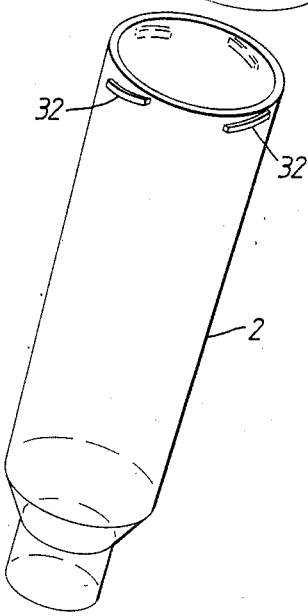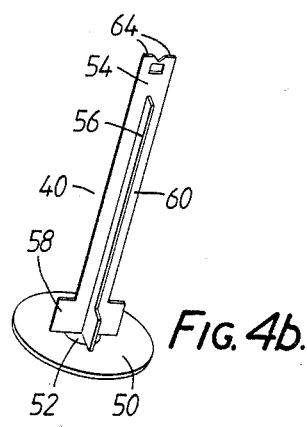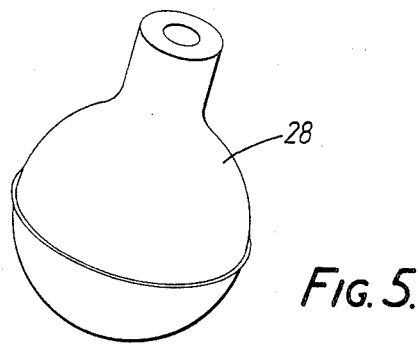

MEDICAL PUMP FOR DEBRIS COLLECTION

BACKGROUND OF THE INVENTION

This invention relates to a pump, which may be suitable for use as a bladder evacuator or for post-operative flushing of blocked catheters, comprising a nozzle for connection by a tube to a bodily or other cavity and a fluid circulator for imposing on fluid within the tube cyclic changes of pressure to cause the fluid to flow alternately and repeatedly into and out of the cavity thereby to flush the cavity, the circulator and the tube being connected by two different fluid flow paths, namely, an efflux path for flow of fluid away from the cavity into a reservoir of the device and thence to the circulator, and a flushing path for flow of liquid from the circulator to the cavity, each of which paths including a non-return valve whereby, in use of the device, fluid flow is uni-directional, from the circulator through the flushing path to the cavity, and then from the cavity through the efflux path back to the circulator.

Such a pump is useful as a bladder evacuator to generate a fluid flow which serves to carry pieces of bodily tissue from the bladder to the reservoir. It is important that the return flow of fluid from the reservoir to the bladder cavity should not carry back as many tissue pieces as have been swept out of the bladder. Some means of concentrating the tissue pieces in the reservoir is required.

The usual circulator employed with bladder evacuators is a rubber bulb, alternately squeezed and released by the surgeon. Any tissue filter introduced into the flushing path for the purpose of confining tissue pieces to the reservoir should restrict the flow of liquid as little as possible so that the frequency of squeezing and release of the bulb can be as high as the surgeon desires. Further, the surface of the filter should not be such as to become blocked by pieces of tissue.

So far as the present applicant is aware, all attempts previous to the present proposal to meet the above requirements have failed to secure wide acceptance by users. A simple bladder evacuator known by the name "Ellik" continues to be the instrument of choice.

The Ellik device has a shape which resembles that of an hour-glass of which the upper chamber is connected to a rubber bulb and the lower chamber is a collection chamber. Alternate squeezing and release of the bulb, when the device is full of liquid, induces outward and return flow of this liquid along a tube connected to the upper chamber of the device and to the bladder of a patient. Debris and other matter entrained in the return flow is collected in the lower chamber.

It is a problem with the Ellik device that it fails to trap all of the entrained matter in the collection chamber. Instead, some of it remains entrained in the liquid flow and is carried back to the bladder. Some at least of the entrained matter is seen to be "tidal", that is to say, carried backwards and forwards between the bladder and the collection chamber.

Proposals for improvement on the performance of the Ellik device are made in U.S. Pat. Nos. 3,892,226 and 4,282,873 published 1975 and 1981 respectively.

U.S. Pat. No. 3,892,226 to Rosen discloses a bladder evacuator which takes the form of a hand-grippable column divided longitudinally by a web into a downflow channel and an upflow channel. At the foot of the column is a reservoir, and at its head is a nozzle and a pumping bulb. In the web at opposite ends are two non-return flap valves, with the one at the foot of the column seating on an area in which is a plurality of small holes instead of one large one, the small holes serving to block the passage of tissue pieces more effectively than a single large hole.

It is one disadvantage of the Rosen device that the area of the seat of the flap valve at the foot of the column is insufficient for effective filtering. If the holes are usefully small they soon become blocked, but if they are made larger they allow small tissue pieces to pass through. Another disadvantage is that the tissue pieces which are caught on the valve seat are not easily cleaned off, are not included with the reservoir when it is removed from the column to enable its contents to be analysed, and may impede movement of the flap valve member and prevent full closure of the valve.

U.S. Pat. No. 4,282,873 to Roth discloses an evacuator with a nozzle, a pumping bulb and a reservoir in which a quarter turn rotation of the bulb causes an integral stem to rotate within a manifold to close one aperture and open another. A combination of squeezing and releasing the bulb with forward and backward rotation of the bulb achieves the desired uni-directional flow including flow through a filter element carried on the manifold, but the co-ordinated hand movements required to operate the device are found in practice to hinder rapid pumping and deter users.

An earlier proposal is to be found in U.S. Pat. No. 1,925,230 to Buckhout. The device offers the major advantages of a large filter area at a location within its reservoir, and non-return valves spaced from the filter, but it is not a convenient instrument to handle and use and therefore does not find favour with users.

A pumping device is disclosed in GB Patent Application No. 2136690A which is relatively convenient to handle, but it lacks an effective filter or uni-directional liquid flow path and so is not well-suited to achieve the sought-for improvement in filtering performance.

SUMMARY OF THE INVENTION

The problem which the present invention addresses is to provide a device which is as convenient to handle and use as the familiar Ellik instrument yet which offers a substantial improvement on its filtering performance.

A pump in accordance with the present invention is characterised in that:

i. the said efflux path and flushing path are disposed one within the other to extend between the circulator and the nozzle;

ii. a hollow filter element is disposed within the efflux path, the filter element having one open end for seating around the circumference of the efflux path at the nozzle end of the path so that the filter element extends along the efflux path from the seating towards the circulator end of the efflux path over a substantial part of the length of the efflux path, whereby liquid may pass through the filter element to the circulator but particulate material may not; and iii. the non-return valve of the efflux path is located between the filter element and the circulator.

Preferably, the said efflux path and flushing path are coaxial.

The filter element and the valve mechanism may conveniently be provided as a replaceable cartridge. The flow of liquid along the efflux path tends to fill the filter element. A contaminated cartridge can be made readily removable by locating one end of the cartridge at an interface of the nozzle and a barrel element housing the cartridge and allowing the nozzle to be readily removable from the barrel. The convenience in use of the barrel element compares favourably with that of the prior Ellik device, but the filtering performance of this barrel element is much better and more certain than that of the Ellik.

The non-return valve of the flushing path may be located between the filter element and the nozzle.

A number of valve configurations are possible. One example is to construct the two valves as a shuttle, having a valve plate at either end. This shuttle may oscillate with alternately one non-return valve plate open and the other non-return valve plate closed.

In another example the two valves may be constructed as a resilient flap member having a resilient flap therein. This flap member and the flap may oscillate so as to open and close the efflux path and flushing path in sequence.

For a better understanding of the invention and to show more clearly how the same may be carried into effect, reference will now be made, by way of example, to the accompanying drawings, in which:

BRIEF DESCRIPTION OF THE DRAWINGS

FIG. 3 is a perspective view of the cartridge of the pump of FIGS. 1 and 2;

FIGS. 4a and 4b are perspective views of the separated parts of a shuttle valve member which can form part of the pump of FIGS. 1 and 2; and FIG. 5 is a perspective exploded view of the outer members of the pump of FIGS. 1 and 2;

DESCRIPTION OF PREFERRED EMBODIMENTS

Figure 1:
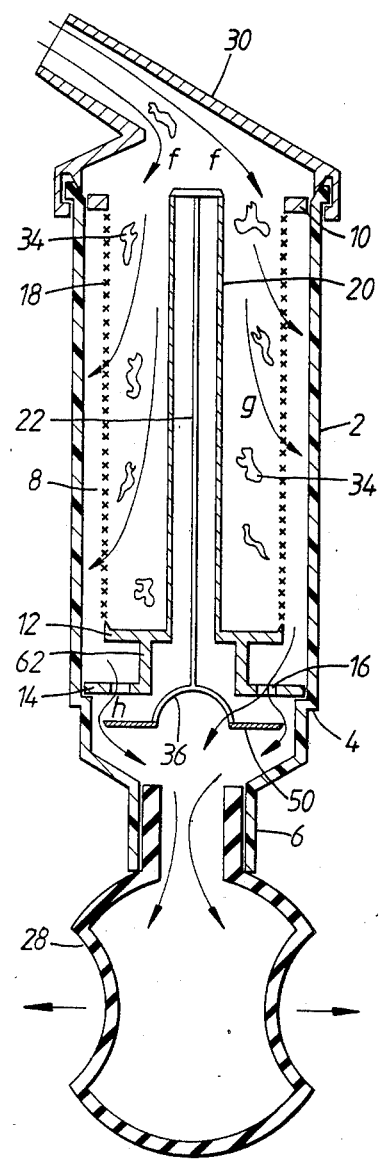
FIGS. 1 and 2 are each a schematic longitudinal section of a first embodiment of a bladder evacuator pump in accordance with the present invention.

The illustrated pump is based on a barrel 2 having a circumferential step 4 near the circulator end 6 of the barrel.

A filter cartridge 8 of circular cross-section includes coaxial filter support discs 10 and 12 and a seating plate 14 having four equally spaced apertures 16 extending therethrough. A filter element 18 is mounted on an dextends between the support discs 10 and 12, and a central tube 20 extends along the length of the filter element 18 from a central aperture in the support disc 12.

Figure 2:
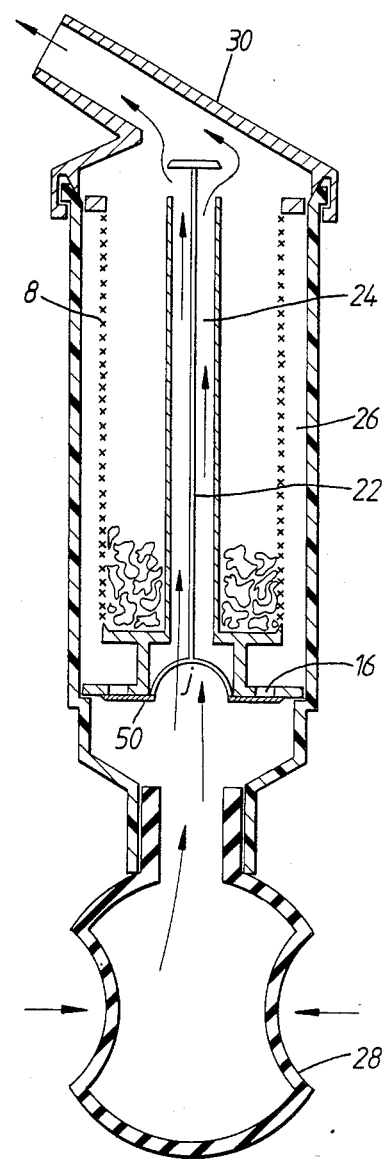
Figures 6, 7:
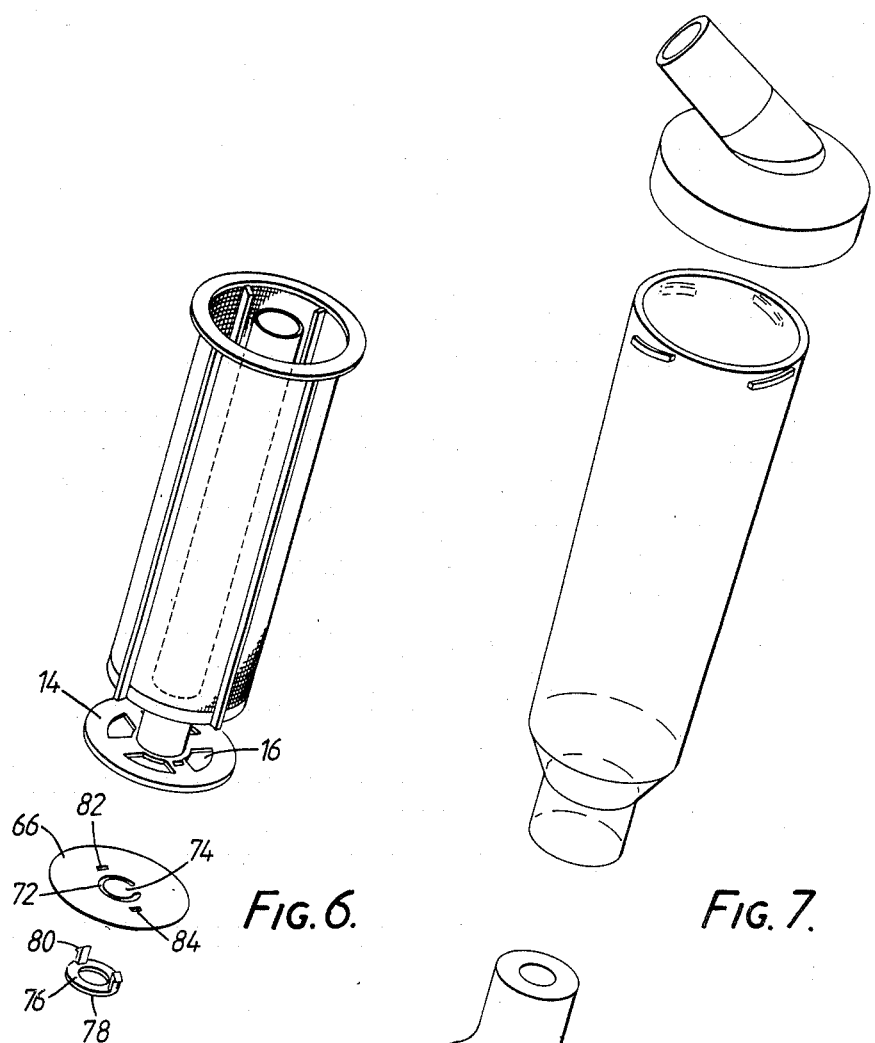
FIG. 6 is an exploded view of the cartridge and valve of a second embodiment of the invention.
FIG. 7 is an exploded view of the outer members of the second embodiment.

FIGS. 1 and 2 illustrate schematically a valve member 22 which shows the principle of operation of a shuttle valve. Referring to the arrows in FIGS. 1 and 2 the central tube 20 separates a relatively small cross-section flushing path 24 from a relatively large cross-section efflux path 26. When the valve member 22 is in its lower end position illustrated in FIG. 1 the valve member closes the central tube 20 to close the flushing path 24 and open the efflux path 26. When the valve member 22 is in its upper end position illustrated in FIG. 2, the valve member closes the apertures 16 in the seating plate 14 to close the efflux path 26 and open the flushing path 24.

A circulator 28 is fitted into a flange at the circulator end 6 of the barrel 2. The seating plate 14 of the filter cartridge 8 rests on the step 4 of the barrel 2, and an intake/discharge nozzle element 30 engages with the cylindrical surface of the barrel 2. This engagement assists in retaining the filter cartridge 8 in position in the barrel 2.

The engagement of the nozzle element 30 and the barrel 2 may be carried out by any convenient means, such as the pin-and-slot bayonet engagement similar to that commonly found in the UK on electric light bulbs, a screw-threaded engagement, or a taper-fit friction engagement.

One suitable manner of engagement is illustrated in FIG. 5 in which the nozzle element 30 is rotated on the barrel 2 and directed into engagement by spaced guide members 32.

To fill the device with sterile liquid the conventional method can be used of immersing the entire device and pumping the circulator 28, which is a bulb, to expel air from inside the device. Alternatively a priming tube can be coupled tot he nozzle element 30 and dipped into a source of the required sterile liquid with the device held vertically. Experience has shown that only about eight full cycles of bulb compression and release are required in order to expel all air from within the device. Once the device is primed, that is, full of sterile liquid, the priming tube is detached from the nozzle element 30, and the nozzle element is then connected to a tube leading to the body cavity to be flushed.

Referring to FIGS. 1 and 2, with the device full of liquid, the nozzle element 30 is connected by a tube full of liquid to a body cavity to be flushed, and the circulator bulb 28 is compressed. Release of the bulb 28 (FIG. 1) allows it to expand and draw liquid f and particualte debris 34 from the body cavity into the efflux path 26. The liquid flows g through the filter element 18 which retains the particulate debris 34 inside the filter element. The valve member 22 is retained in its lower end position by the liquid flow through the nozzle element 30 and along the efflux path 26 so as to close the flushing path 24 as illustrated in FIG. 1. The liquid then flows h through the apertures 16 into the circulator bulb 28.

The valve member 22 includes a lower valve plate 50 having a central hole therein, and a stirrup 36.

Referring to FIG. 2, squeezing the bulb 28 causes the valve member 22 to cover the apertures 16 so as to close the efflux path 26 and open the flushing path 24. This squeezing of the bulb 28 also causes liquid to flow j through the central hole in the lower valve plate 50 of the valve member 22, past the stirrup 36, along the flushing path 24, through the nozzle element 30 and into the body cavity. There is no back flow in the efflux path 26 to disturb the debris particles 34 which have collected in the lower region of the filter element 18. Release of the bulb 28 repeats the aforementioned operational cycle which will probably increase the amount of particualte debris 34 in the filter element 18.

Conveniently at least the barrel 2 is made of a transparent plastics material. The efflux path 26 constitutes a reservoir of the pump, from which the bulb 28 can draw when released after compression. This reservoir does not however function, as in the Ellik device, as a settling tank for particulate debris 34. This debris is instead retained in the filter element 18.

One important advantage of this embodiment is that the filter cartridge 8 and the valve member 22 can conveniently be discarded after use and replaced thereby considerably reducing the work of cleaning.

To assist the assembly of the valve member 22 in the filter cartridge 8, this valve member 22 can be manufactured for example in two easily assembled parts 38 and 40 illustrated in FIGS. 4a and 4b respectively. The part 38 has a cap 42 to close the upper end of the central tube 20, and a longitudinal plate 44 having an aperture 46 therein. Two fins 48 project along part of the plate 44; the plate 44 and the fins 48 being dimensioned to ensure that the part 38 makes a sliding fit in the tube 20.

The valve member part 40 includes a plate 50, having a central aperture 52 therein, a plate 54 and fins 56 which are perpendicular to one another, and which extend longitudinally from the plate 50. The plate 54 and the fins 56 are stepped tohave portions 58 and 60 adjacent to and remote from the plate 50 respectively. The plate 50 is dimensioned to close the apertures 16 when the valve member 22 is in its upper end position ilustrated in FIG. 2. The portions 58 and 60 are dimensioned to make a sliding fit in the shaft 62 of the filter cartridge 8, and in the central tube 20 respectively. Two prongs 64 extend into contact with one another at the opposite end of the plate 54 to the plate 50. To assemble the valve member, the valve member parts 38 and 40 are pushed into the central tube 20 and shaft 62 respectively until the prongs 64 are firstly parted by the plate 44 and then snap shut in the aperture 46 to retain the valve member parts 28 and 40 in contact with one another to form a single valve member.

When the valve member is in the lower end position illustrated in FIG. 1, the cap 42 closes the central tube 20 to close the flushing path 24. When the valve member is in the upper end position illustrated in FIG. 2 the plate 50 is in contact with the seating plate 14 to close the apertures 16 thereby closing the efflux path 26. Liquid can pass from the circulator bulb 28 through the aperture 52 in the plate 50 and along the central tube 20 to return to the body cavity.

The valve member parts 38 and 40 can be made of any suitable material, such as for example a suitable plastics material. The filter cartridge 8 and the valve member parts 38 and 40 are simple to manufacture and assemble, and are particularly advantageous when it is desirable to remove and replace a filter cartridge and valve member after use.

Referring to FIGS. 6 to 9 a second embodiment of the invention includes a valve member different from the valve member of the first embodiment. The other components of the second embodiment are the same as the other components of the first embodiment and for clarity corresponding components of the two embodiments will be given the same reference numerals.

Figures 8, 9:
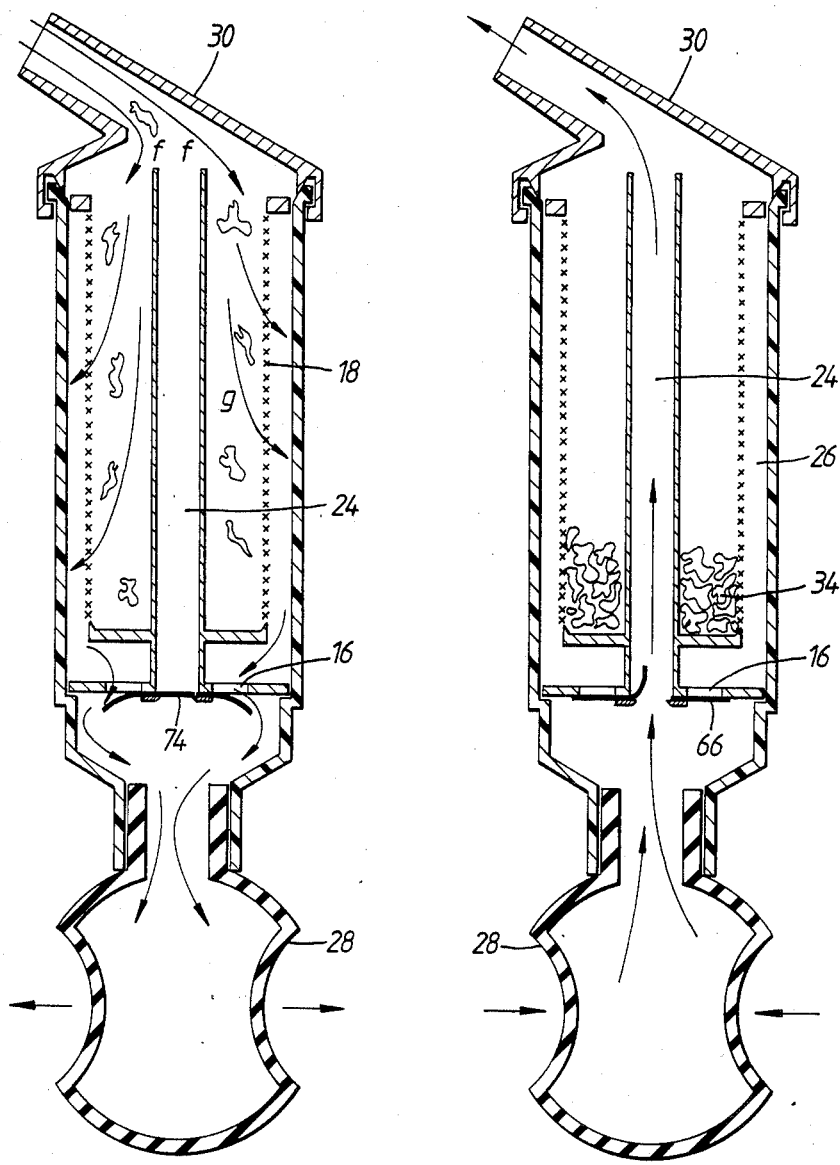
FIGS. 8 and 9 are each a schematic longitudinal section of the second embodiment.

The valve member of the second embodiment includes a circular flap member 66 arranged to be mounted immediately below the seating plate 14. The flap member 66 is dimensioned so that when mounted it extends radially beyond the apertures 16 as illustrated in FIG. 9. This flap member is made of any suitable resilient material, such as for example latex, thermoplastic or silicone rubber.

A horse shoe shaped cut 72 is made in the flap member 66 to define a central flap 74. A plastics retaining clip 76 includes a circular base 78 of slightly smaller internal diameter than the flap 74, and two up standing studs 80 dimensioned to make a clip fit through corresponding locating holes 82 and 84 in the flap member 66 and into the seating plate 14 respectively to mount the flap members 66 on the seating plate 14.

Referring to FIGS. 8 and 9 the operation of this second embodiment is similar to the operation of the first embodiment.

The device is primed by filling it with sterile liquid as previously described.

With the device full of liquid the nozzle element 30 is connected by a tube full of liquid to a body cavity be flushed, and the bulb 28 is compressed.

Referring to FIG. 9, compressing or squeezing the bulb 28 causes the flap member 66 to cover the apertures 16 so as to close the efflux path 26, and causing the flap 74 to open thereby opening the flushing path 24. As with the first embodiment, this squeezing of the bulb 28 also causing liquid to flow through the device into the body cavity. There is no back flow in the efflux path 26 to disturb the debris particulars 34 which have collected in the lower region of the filter element 18.

Release of the bulb 28 allows it to expand and draw liquid f and particulate debris 34 from the body cavity into the efflux path 26. The pressure conditions caused by this release of the bulb 28 causes the flap 74 to close the flushing path 24 and the outer region of the flap member 66 to open the apertures 16. The liquid flows g through the element 18 which retains the particulate debris 34 inside the filter element. The flap 74 is retained in its lower closed position by the pressure of fluid above it so as to close the flushing path 24 as illustrated in FIG. 8. The liquid then flows through the aperture 16 into the circular bulb 28.

The flap member 66, including the flap 74 can be made of any suitable flexible material.

In one example of the invention, the device is constructed as a sterile single use product.

I claim:

1. A pump for fluid recirculation and debris collection comprising a nozzle for both intake and discharge for connection by tube to a bodily or other cavity, and a fluid circulator for imposing on fluid within the tube cyclic changes of pressure to cause the fluid to flow alternately and repeatedly into and out of the cavity thereby to flush the cavity, an elongate barrel extending between and joining the circulator and the nozzle, two different fluid flow paths within said barrel and connecting said circulator and said nozzle, namely, an efflux path including a reservoir for flow of fluid away from the cavity into the reservoir of the device and thence to the circulator, and a flushing path for a flow of fluid from the circulator to the cavity, each of which paths including a non-return valve whereby, in use of the device, fluid flow is uni-directional from the circulator through the flushign path to the cavity, and thence from the cavity through the efflux path back to the circulator, the said efflux path and flushing path are disposed one within the other with one path peripherally surrounding the other path between the circulator and the nozzle, a hollow filter element is disposed within the efflux path with the barrel for removal of debris from the flow away from the cavity, the filter element having one open end seating around the circumference of the efflux path at the nozzle end of the path for free flow of the fluid therein from the cavity, the filter element extending along the efflux path from the seating towards the circulator end of the efflux path over a major part of the length of the efflux path, said filter element confining the debris while allowing passage of fluid flow through the filter element to the circulator, and the nonreturn valve of the efflux path being located between the filter element and the circulator and downstream of the confined debris, said filter element and said non-return valves comprising a replaceable cartridge within said barrel.

2. A pump as claimed in claim 1 in which the efflux path and flushing path are coaxial with one another.

3. A pump as claimed in claim 1 in which the nozzle is readily removable from the barrel.

4. A pump as claimed in claim 1 in which the two valves are constructed as a shuttle having a valve plate at either end, said shuttle including means connecting the valve plates for movement of the valve plates in unison.

5. A pump as claimed in claim 1 including a valve seating having apertures located in the efflux path and flushing path, the two valves comprising a resilient flap member having a resilient flap therein, said flap member being located on the valve seating said flap member comprising one of said valves and being operable independently of said flap therein, said flap comprising the other valve and being operable independently of said flap member.

6. A pump as claimed in claim 5 in which the flap is operable to close the aperture in the flushing path and the flap member is operable to close the aperture in the efflux path.

7. A pump as claimed in claim 5 in which the flap member is substantially circular, and the flap is located centrally therein.

8. A pump as claimed in claim 5 in which the flap member and flap are made of latex, theremoplastic or silicone rubber.

9. A pump as claimed in claim 1 wherein said cartridge includes a first support disc at said one end at the interface of the nozzle and the barrel, and a second support disc longitudinally remote from the first support disc, said filter element engaging and mounting between said support discs, a seating plate longitudinally outward of said second support disc to the opposite side thereof from said first support disc, said seating plate being positioned adjacent said circulator and defining a second end of the cartridge, and central tube means extending axially through said seating plate and support discs for the full height of said cartridge, said tube means defining said fluid flow paths, one internally of said tube means and one exteriorly thereof between said tube means and the barrel thereabout.

10. A pump as claimed in claim 9 wherein said filter element surrounds said tube means in outwardly spaced relation thereto and in inwardly spaced relation to the barrel element thereabout, said efflux path being exterior of said tube means.

11. A pump as claimed in claim 10 including a first valve opening through said seating plate exterior of said tube means, said tube means, at said seating plate, defining a second valve opening, said non-return valves comprising a flap member overlying said seating plate and the valve openings, said flap member including a first portion overlying the first valve opening and moveable to open said first valve opening in response to flow in said efflux path exterior of said tube mans, and a second portion overlying the second valve opening and moveable to open said second valve opening in response to flow in said flushing path interior of said tube means.

12. A pump for fluid recirculation and debris collection comprising a nozzle for both intake and discharge for connection by tube to a bodily or other cavity, and a fluid circulator for imposing on fluid within the tube cyclic changes of pressure to cause the fluid to flow alternately and repeatedly into and out of the cavity thereby to flush the cavity, the circulator and the nozzle being connected by two different fluid flow paths, namely, an efflux path including a reservoir for flow of fluid away from the cavity into the reservoir of the device and thence to the circulator, and a flushing path for a flow of fluid from the circulator to the cavity, each of which paths including a non-return valve whereby, in use of the device, fluid flow is uni-directional from the circulator through the flushing path to the cavity, and thence from the cavity through the efflux path back to the circulator, the said efflux path and flushing path are disposed one within the other between the circulator and the nozzle, a hollow filter element is disposed within the efflux path for removal of debris from the flow away from the cavity, the filter element having one open end seating around the circumference of the efflux path at the nozzle end of the path for flow of the fluid therein from the cavity, the filter element extending along the efflux path from the seating towards the circulator end of the efflux path over a substantial part of the length of the efflux path, said filter element confining the debris while allowing passage of fluid flow through the filter element to the circulator, the non-return valve of the efflux path being located between the filter element and the circulator, the two valves being constructed as a shuttle having a valve plate at either end, the shuttle being operable to oscillate with alternately one non-return valve plate open and the other non-return valve plate closed.

13. A pump for fluid recirculation and debris collection comprising a nozzle for both intake and discharge for connection by tube to a bodily or other cavity, and a fluid circulator for imposing on fluid within the tube cyclic changes of pressure to cause the fluid to flow alternately and repeatedly into and out of the cavity thereby to flush the cavity, an elongate barrel extending between and joining the circulator and the nozzle, two different fluid flow paths within said barrel and connecting said circulator and said nozzle, namely, an efflux path including a reservoir for flow of fluid away from the cavity into the reservoir of the device and thence to the circulator, and a flushing path for a flow of fluid from the circulator to the cavity, each of which paths including a non-return valve whereby, in use of the device, fluid flow is uni-directional from the circulator through the flushing path to the cavity, and thence from the cavity through the efflux path back to the circulator, the said efflux path and flushing path are disposed one within the other with one path peripherally surrounding the other path between the circulator and the nozzle, a hollow filter element is disposed within the efflux path within the barrel for removal of debris from the flow away from the cavity, the filter element having one open end seating around the circumference of the efflux path at the nozzle end of the path for free flow of the fluid therein from the cavity, the filter element extending along the efflux path from the seating towards the circulator end of the efflux path over a substantial part of the length of the efflux path, said filter element confining the debris while allowing passage of fluid flow through the filter element to the circulator, the non-return valve of the efflux path being located between the filter element and the circulator and downstream of the confined debris, and a valve seating having apertures located in the efflux path and flushing path, the two valves comprising a resilient flap member having a resilient flap therein, said flap member being located on the valve seating said flap member comprising one of said valves and being operble independently of said flap therein, said flap comprising the other valve and being operable independently of said flap member.

14. A pump as claimed in claim 13 wherein the flap member is substantially circular, and the flap is located centrally therein.

* * * * *